US00PP28182P3

(12) United States Plant Patent
Pieters

(10) Patent No.: US PP28,182 P3
(45) Date of Patent: Jul. 11, 2017

(54) CHRYSANTHEMUM PLANT NAMED 'THERA RED'

(50) Latin Name: *Chrysanthemum×morifolium*
Varietal Denomination: Thera Red

(71) Applicant: Dirk Pieters, Oostnieuwkerke (BE)

(72) Inventor: Dirk Pieters, Oostnieuwkerke (BE)

(73) Assignee: Paraty B.V.B.A., Oostnieuwkerke (BE)

( * ) Notice: Subject to any disclaimer, the term of this patent is extended or adjusted under 35 U.S.C. 154(b) by 141 days.

(21) Appl. No.: 14/545,965

(22) Filed: Jul. 10, 2015

(65) Prior Publication Data

US 2017/0013759 P1 Jan. 12, 2017

(51) Int. Cl.
*A01H 5/02* (2006.01)

(52) U.S. Cl.
USPC ..... Plt./293

(58) Field of Classification Search
USPC ..... Plt./263.1, 286, 287, 293
See application file for complete search history.

*Primary Examiner* — Susan McCormick Ewoldt
*Assistant Examiner* — Karen Redden
(74) *Attorney, Agent, or Firm* — C. A. Whealy

(57) ABSTRACT

A new and distinct cultivar of *Chrysanthemum* plant named 'Thera Red', characterized by its upright, outwardly spreading and uniformly rounded plant habit; moderately vigorous growth habit; freely branching habit; dense and full plant habit; dark green-colored leaves; uniform and freely flowering habit; and relatively small decorative-type inflorescences with dark red-colored ray florets.

1 Drawing Sheet

Botanical designation: *Chrysanthemum×morifolium.*
Cultivar denomination: 'THERA RED'.

BACKGROUND OF THE INVENTION

The present invention relates to a new and distinct cultivar of *Chrysanthemum* plant, botanically known as *Chrysanthemum×morifolium* and hereinafter referred to by the name 'Thera Red'.

The new *Chrysanthemum* plant is a product of a planned breeding program conducted by the Inventor in Oostnieuwkerke, Belgium. The objective of the breeding program is to create new uniformly mounding and freely flowering *Chrysanthemum* plants with unique and attractive ray floret coloration.

The new *Chrysanthemum* plant originated from a cross-pollination made by the Inventor in Oostnieuwkerke, Belgium in October, 2009 of *Chrysanthemum×morifolium* 'Belgo Red', not patented, as the female, or seed, parent with *Chrysanthemum×morifolium* 'Tirona Red', not patented. The new *Chrysanthemum* plant was discovered and selected by the Inventor as a flowering plant from within the progeny of the stated cross-pollination in a controlled greenhouse environment in Oostnieuwkerke, Belgium in September, 2010.

Asexual reproduction of the new *Chrysanthemum* plant by vegetative terminal cuttings was first conducted in a controlled greenhouse environment in Oostnieuwkerke, Belgium in January, 2011. Asexual reproduction by vegetative terminal cuttings has shown that the unique features of this new *Chrysanthemum* plant are stable and reproduced true to type in successive generations.

SUMMARY OF THE INVENTION

Plants of the new *Chrysanthemum* have not been observed under all possible combinations of environmental conditions and cultural practices. The phenotype may vary somewhat with variations in environmental conditions such as temperature, daylength and light intensity, without, however, any variance in genotype.

The following traits have been repeatedly observed and are determined to be the unique characteristics of 'Thera Red'. These characteristics in combination distinguish 'Thera Red' as a new and distinct *Chrysanthemum* plant:

1. Upright, outwardly spreading and uniformly rounded plant habit; moderately vigorous growth habit.
2. Freely branching habit; dense and full plant habit.
3. Dark green-colored leaves.
4. Uniform and freely flowering habit.
5. Relatively small decorative-type inflorescences with dark red-colored ray florets.

Plants of the new *Chrysanthemum* differ from the female parent, 'Belgo Red', in the following characteristics:

1. Plants of the new *Chrysanthemum* are more uniformly rounded than and not as upright as plants of 'Belgo Red'.
2. Plants of the new *Chrysanthemum* have larger leaves than plants of 'Belgo Red'.
3. Plants of the new *Chrysanthemum* have smaller inflorescences than plants of 'Belgo Red'.
4. Plants of the new *Chrysanthemum* and 'Belgo Red' differ in ray floret color as inflorescences of plants of 'Belgo Red' have pale red-colored ray florets.

Plants of the new *Chrysanthemum* differ from the male parent, 'Tirona Red', in the following characteristics:

1. Plants of the new *Chrysanthemum* are not as vigorous as plants of 'Tirona Red'.
2. Plants of the new *Chrysanthemum* have larger inflorescences than plants of 'Tirona Red'.
3. Plants of the new *Chrysanthemum* and 'Tirona Red' differ in ray floret color as inflorescences of plants of 'Tirona Red' have faded red-colored ray florets.

Plants of the new *Chrysanthemum* can be compared to plants of *Chrysanthemum×morifolium* 'Pavia Red', disclosed in U.S. Plant Pat. No. 23,134. In side-by-side comparisons conducted in Oostnieuwkerke, Belgium, plants of the new *Chrysanthemum* differed from plants of 'Pavia Red' in the following characteristics:

1. Plants of the new *Chrysanthemum* were more compact than plants of 'Pavia Red'.
2. Leaves of plants of the new *Chrysanthemum* were smaller and not as dark green in color as leaves of plants of 'Pavia Red'.
3. Plants of the new *Chrysanthemum* and 'Pavia Red' differed in ray floret color as inflorescences of plants of 'Pavia Red' had red purple-colored ray florets.

BRIEF DESCRIPTION OF THE PHOTOGRAPH

The accompanying photograph illustrates the overall appearance of the new *Chrysanthemum* plant showing the colors as true as it is reasonably possible to obtain in colored reproductions of this type. Colors in the photograph may differ slightly from the color values cited in the detailed botanical description which accurately describe the colors of the new *Chrysanthemum* plant.

The photograph comprises a side perspective view of a typical flowering plant of 'Thera Red' grown in a container.

DETAILED BOTANICAL DESCRIPTION

The aforementioned photograph and following observations and measurements describe plants grown in 19-cm containers in an outdoor nursery in Oostnieuwkerke, Belgium during the spring and summer and under cultural practices generally used in commercial *Chrysanthemum* production. During the production of the plants, day temperatures ranged from 18° C. to 21° C. and night temperatures ranged from 10° C. to 15° C. Plants were 20 weeks old when the photograph and description were taken. In the following description, color references are made to The Royal Horticultural Society Colour Chart, 2005 Edition, except where general terms of ordinary dictionary significance are used.

Botanical classification: *Chrysanthemum×morifolium* 'Thera Red'.

Parentage:

*Female, or seed, parent.*—*Chrysanthemum×morifolium* 'Belgo Red', not patented.

*Male, or pollen, parent.*—*Chrysanthemum×morifolium* 'Tirona Red', not patented.

Propagation:

*Type.*—Vegetative terminal cuttings.

*Time to initiate roots, summer.*—About 14 days at temperatures about 20° C.

*Time to initiate roots, winter.*—About 20 days at temperatures about 20° C.

*Time to produce a rooted young plant, summer.*—About 30 days at temperatures about 20° C.

*Time to produce a rooted young plant, winter.*—About 40 days at temperatures about 20° C.

*Root description.*—Fine, fibrous; typically light brown in color, actual color of the roots dependent on substrate composition, water quality, fertilizers, substrate temperature and age of roots.

*Rooting habit.*—Freely branching; medium density.

Plant description:

*Appearance.*—Perennial decorative-type *Chrysanthemum*; stems upright and outwardly spreading giving a uniformly rounded appearance to the plant; plants nearly spherical in overall, shape; very freely branching habit, about 25 primary lateral branches develop, each primary lateral branch with multiple secondary branches; pinching enhances lateral branch development; dense and full plant habit; moderately vigorous growth habit.

*Plant height.*—About 35 cm.

*Plant width.*—About 50 cm.

*Lateral branches.*—Length: About 25 cm. Diameter: About 2 mm to 3 mm. Internode length: About 1.5 cm. Strength: Strong, flexible. Aspect: Upright to outwardly spreading. Texture: Pubescent; longitudinally ridged. Luster: Matte. Color: Close to 144A.

*Leaves.*—Arrangement: Alternate, simple. Length: About 2.5 cm to 4.5 cm. Width: About 1.5 cm to 3 cm. Apex: Rounded to cuspidate. Base: Attenuate. Margin: Palmately lobed and serrate, sinuses between lateral lobes divergent to parallel. Texture, upper and lower surfaces: Slightly pubescent. Luster, upper and lower surfaces: Matte. Color: Developing leaves, upper surface: Close to 139C. Developing leaves, lower surface: Close to 137D. Fully expanded leaves, upper surface: Close to N137C; venation, close to 148C. Fully expanded leaves, lower surface: Close to 147B; venation, close to 147B to 147C. Petioles: Length: About 1 cm. Diameter: About 2 mm. Texture, upper and lower surfaces: Slightly pubescent and slightly rough. Luster, upper and lower surfaces: Matte. Color, upper surface: Close to 146C. Color, lower surface: Close to 146D.

Inflorescence description:

*Appearance.*—Decorative-type inflorescence form; inflorescences borne on terminals above foliar plane; disc and ray florets arranged acropetally on a capitulum.

*Fragrance.*—Faintly fragrant, pungent.

*Flowering time.*—Under natural season conditions, plants flower in early October in Belgium.

*Postproduction longevity.*—Inflorescences maintain good color and substance for about five weeks on the plant grown in an outdoor nursery; inflorescences persistent.

*Quantity of inflorescences.*—Freely flowering habit with about 20 inflorescences developing per lateral branch with numerous inflorescences developing per plant.

*Inflorescence buds.*—Height: About 4 mm. Diameter: About 7 mm. Shape: Globular. Texture: Smooth. Color: Close to 144A and 137C.

*Inflorescence size and shape.*—Diameter: Relatively small, about 2 cm. Depth (height): About 3.5 cm. Disc diameter: About 1 mm. Shape: Circular; raised dome. Receptacle diameter: About 3 mm. Receptacle height: About 2.5 mm to 3 mm. Receptacle texture: Smooth, glabrous. Receptacle color: Close to 144B.

*Ray florets.*—Quantity and arrangement: About or more than 200 ray florets per inflorescence arranged in about ten whorls. Length: About 7 mm to 10 mm. Width: About 4 mm. Shape: Oval. Apex: Rounded. Base: Attenuate. Margin: Entire. Aspect: Mostly flat. Texture, upper and lower surfaces: Smooth, glabrous. Luster, upper and lower surfaces: Matte. Color: When opening and fully opened, upper surface: Close to 53A; color does not fade with development. When opening and fully opened, lower surface: Close to 185B; color does not fade with development.

*Disc florets.*—Quantity and arrangement: About 20 or less disc florets per inflorescence and massed at the center of the receptacle; disc florets inconspicuous. Length: About 3 mm. Diameter: About 0.5 mm to 1 mm. Shape: Tubular, elongated; apices acute. Color, immature: Apex: Close to 144C. Mid-section: Close to 5B. Base: Close to 145D. Color, mature: Apex: Close to 12A. Mid-section: Close to 12A. Base: Close to 12A.

*Phyllaries.*—Quantity and arrangement: About 25 phyllaries per inflorescence arranged in about two or three whorls. Length: About 4 mm to 6 mm. Width: About 2 mm to 3 mm. Shape: Ovate. Apex: Rounded. Base: Rounded to truncate. Margin: Entire. Texture, upper and lower surfaces: Smooth, glabrous. Luster, upper and lower surfaces: Matte. Color, upper surface: Close to 137A. Color, lower surface: Close to N137B.

*Peduncles.*—Length, terminal peduncle: About 4 cm. Length, fourth peduncle: About 6 cm. Length, seventh peduncle: About 8 cm. Diameter: About 2 mm. Angle: About 30° from vertical. Strength: Moderately strong. Texture: Slightly pubescent. Luster: Matte. Color: Close to 146B.

*Reproductive organs.*—Androecium: None observed. Gynoecium: None observed.

*Seeds and fruit.*—Seed and fruit production have not been observed on plants of the new *Chrysanthemum.*

Disease & pest resistance: Resistance to pathogens and pests common to *Chrysanthemum* plants has not been observed on plants of the new *Chrysanthemum* grown under commercial production conditions.

Garden performance: Plants of the new *Chrysanthemum* have demonstrated excellent garden performance and will tolerate temperatures ranging from about 0° C. to about 45° C.

It is claimed:

1. A new and distinct *Chrysanthemum* plant named 'Thera Red' as illustrated and described.

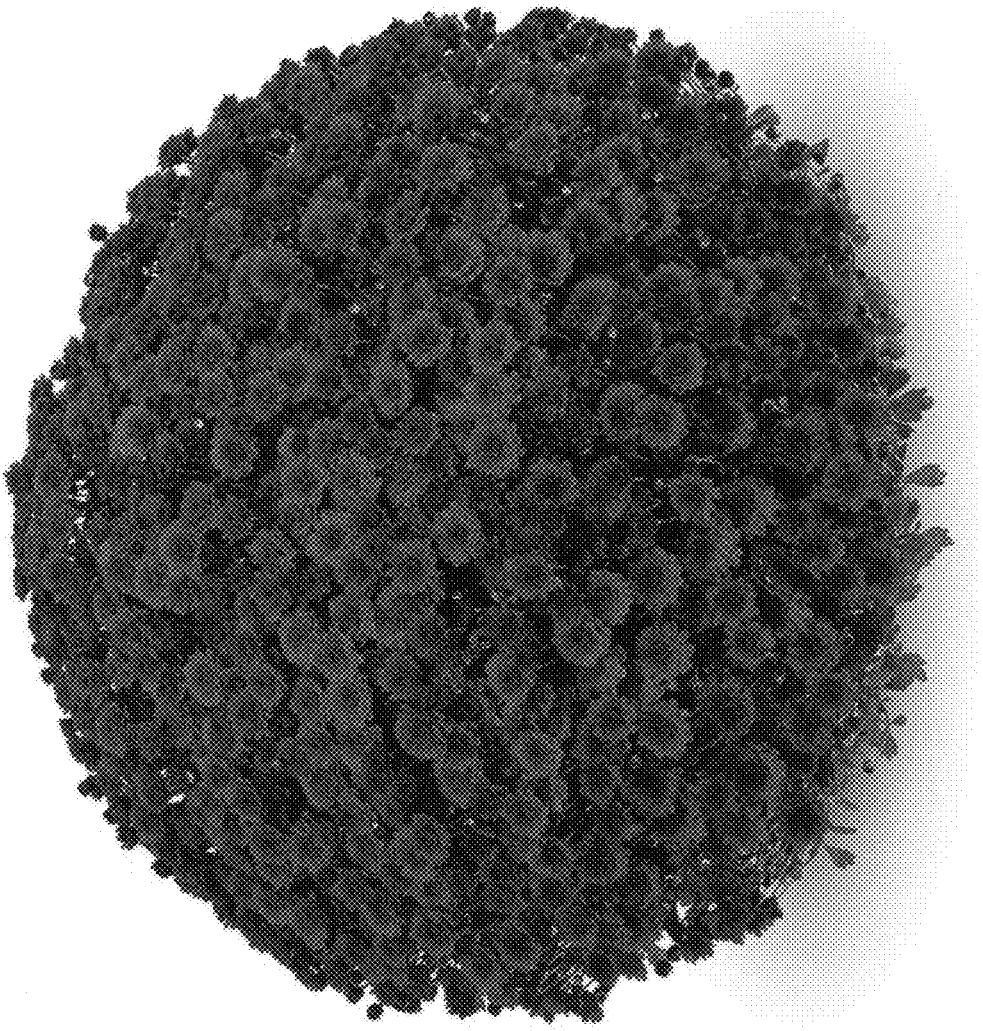

* * * * *